United States Patent
Kim et al.

(10) Patent No.: US 10,927,219 B2
(45) Date of Patent: Feb. 23, 2021

(54) CROSSLINKED SILSESQUIOXANE RANDOM COPOLYMERS ABSORBING BOTH UVA AND UVB AND METHOD FOR PREPARING THE SAME

(71) Applicant: NANO AND MICRO TECHNOLOGIES CO., LTD., Daejeon (KR)

(72) Inventors: Veronica Kim, Grafton, MA (US); Ji Woong Kim, Daejeon (KR)

(73) Assignee: NANO AND MICRO TECHNOLOGIES CO., LTD., Daejeon (KR)

( * ) Notice: Subject to any disclaimer, the term of this patent is extended or adjusted under 35 U.S.C. 154(b) by 121 days.

(21) Appl. No.: 16/314,176

(22) PCT Filed: Jun. 30, 2017

(86) PCT No.: PCT/KR2017/006947
§ 371 (c)(1),
(2) Date: Dec. 28, 2018

(87) PCT Pub. No.: WO2018/004292
PCT Pub. Date: Jan. 4, 2018

(65) Prior Publication Data
US 2019/0202994 A1    Jul. 4, 2019

(30) Foreign Application Priority Data

Jun. 30, 2016    (KR) .................. 10-2016-0082667

(51) Int. Cl.
*C08L 83/08*    (2006.01)
*C08G 77/26*    (2006.01)
(Continued)

(52) U.S. Cl.
CPC .............. *C08G 77/26* (2013.01); *A61K 8/898* (2013.01); *A61Q 19/00* (2013.01); *C08L 83/08* (2013.01); *A61Q 17/04* (2013.01); *C08L 2312/08* (2013.01)

(58) Field of Classification Search
None
See application file for complete search history.

(56) References Cited

U.S. PATENT DOCUMENTS 8,921,505 B2 * 12/2014 Kim .................. A61K 8/025
528/14
2007/0249854 A1 * 10/2007 Kim .................. A61K 8/02
556/419

FOREIGN PATENT DOCUMENTS

KR    10-2005-0105545    11/2005
KR    10-2005-0105567    11/2005
(Continued)

OTHER PUBLICATIONS

Chambers et al. "Excited State Dynamics in the Structural Characterization of Solid Alkyltrimethoxysilane-Derived Sol-Gel Films and Glasses Containing Bound or Unbound Chromophores" Chem. Mater. 1994, 6, 1351-1357. (Year: 1994).*

(Continued)

*Primary Examiner* — Robert S Loewe
(74) *Attorney, Agent, or Firm* — Kile Park Reed & Houtteman PLLC

(57) ABSTRACT

The present invention relates to crosslinked silsesquioxane random copolymers absorbing both UVA and UVB although they contain only UVB absorbing chromophores, and methods preparing the same. Crosslinked polysilsesquioxane random copolymers prepared by the method of the present invention have good sensory and are safe as they are not absorbed into human body due to their high molecular weights. These polymers have desirable UV blocking func- (Continued)

tion as they absorb wider range of UV including both UV B (280-320 nm) and UV A (320-400 nm) by excimer or exciplex formation between chromophores. Also, these polymers are useful for UV blocking cosmetics as they do not develop opaque white appearance in high concentration (30%).

22 Claims, 6 Drawing Sheets

(51) Int. Cl.
*A61Q 19/00* (2006.01)
*A61K 8/898* (2006.01)
*A61Q 17/04* (2006.01)

(56) References Cited

FOREIGN PATENT DOCUMENTS

| KR | 10-2012-0007922 | 1/2012 |
| KR | 10-2012-0042397 | 5/2012 |

OTHER PUBLICATIONS

Kim et al. "Preparation and Characterization of Polysilsesquioxane Particles Containing UV-Absorbing Groups" Macromeolecular Research, 20, 2012, 437-446. (Year: 2012).*

Howells et al. "Steady-State Fluorescence of Dye-Sensitized TiO2 Xerogels and Aerogels as a Probe for Local Chromophore Aggregation" J. Phys. Chem. A 2003, 107, 3300-3304. (Year: 2003).*

International Search Report for International Application No. PCT/KR2017/006947; dated Oct. 31, 2017.

Punnipa Kidsaneepoiboon et al., "Organic-inorganic hybrid polysilsesquioxane nanospheres as UVA/UVB absorber and fragrance carrier"; Journal of Materials Chemistry, Jun. 14, 2011, vol. 21, No. 22, pp. 7922-7930.

* cited by examiner

- ● Crosslinking point
- ○ Microstructure controller
- ▭ Excimer

CROSSLINKED SILSESQUIOXANE RANDOM COPOLYMERS ABSORBING BOTH UVA AND UVB AND METHOD FOR PREPARING THE SAME

BACKGROUND OF THE INVENTION

Field of Invention

This application claims priority to and the benefit of Korean Patent Application No. 10-2016-0082667 filed in the Korean Intellectual Property Office on 30 Jun. 2016, the disclosure of which are incorporated herein by reference.

The present invention relates to crosslinked silsesquioxane random copolymers prepared from polysilsesquioxane monomer containing only UV B absorbing chromophores but absorb both UVA and UVB and a method for preparing same.

Description of the Related. Art

Excess expose to sunlight is known to cause various damages to skin such as sunburn and skin cancer. In order to prevent skin damages, cosmetic products that contain UV absorbing organic and inorganic compounds with low known toxicity have been developed that are called sunscreens. Recently, usage of sunscreen is expanding in applications and amounts and sunscreen ingredients are now added to general purpose cosmetics such as lipsticks. Currently, 29 compounds are approved in Korea as UV ingredients including three powdery products, (i) 2, 2'-[6-(4-ethoxyphenyl)-1,3,5-triazine-2,4-diyl]bis{5-[(2-(ethyl hexyl)oxy]phenol] (commercial name: Tinosorb S) that is an organic ingredient, (ii) titania, and (iii) zinc oxide that are inorganic ingredients. Other products are generally liquid or solid with low melting temperature that are present as liquid in cosmetics. It has been already known that low molecular weight liquid ingredients in cosmetics are absorbed through skin. Organic UV ingredients are expected to be found in urine and breast milk samples of users, and indeed UV ingredients were found to be absorbed through skin. In addition to their inherent adverse effects such as disturbing endocrine system, sunscreen ingredients undergo photoreaction to produce radicals. Considering the purpose of applying sunscreens on skin, it is impossible not to be exposed to sun light with sunscreens on the skin while UV ingredients penetrate skin and produce radicals. Consequently, there are opinions that sunscreens induce skin cancers rather than prevent them. Furthermore, there have not been sufficient reliable studies on long-term adverse effects of sunscreen ingredients including accumulation of them in human body. Consequently, a great deal of concerns on sunscreens are raised.

Contrastingly, inorganic powders, titania and zinc oxide, are not soluble in water or common organic solvents, there is no possibility for them to penetrate skin and they are considered to be the safest UV ingredients. However, when mixed with other materials, their high refractive indices develop white appearance on the skin and cause rough feeling of cosmetics. Moreover, powders of large sizes give poor UV protection, they are produced in sizes smaller than 100 nm or nano sizes. Nano sized titania powders are widely used as photo-catalyst because they have high photo-reactivity of degrading organic compounds nearby when irradiated with UV light. Applying uncoated particles with such properties on skin may cause damages when they are in direct contact also even if they are in direct contact with skin, titanium dioxide nano particles can greatly enhance formation of reactive oxygen species (ROS). Furthermore, these particles are so small that it may be difficult to wash off thoroughly. The particles remaining on skin may cause further adverse effects.

In addition, although reducing particle sizes to nano sizes has the advantage of reducing the intensity of white appearance on skin, nano particles instead cause ghostly blue appearance that is considered to be unfavorable for cosmetics. Powders smaller than 2.5 micrometer are classified as carcinogen, and even smaller nano particles are found to get into human body through blood stream that raises even serious concerns on human health.

In order to reduce adverse effects of titania nano powders, various materials are coated on them but problems of small sizes and poor sensory have not been significantly solved. These disadvantageous properties limit the use of these particles and when used, contents of them in cosmetics are usually lower than 10% although they are allowed to be used in higher concentrations in many countries. In order to resolve problems of titania and zinc oxide nanoparticles further, silica and poly(methyl methacrylate) spheres where titania and zinc oxide nanoparticles are embedded have been commercialized. However, such products are not widely used as their UV protecting efficacy is low and they still develop white appearance.

In a more advanced method, polysilsesquioxanes, one type of different poly(organosilicon oxide)s, containing p-methoxycinnamic acid was synthesized. These polysilsesquioxanes powders are hybrids of organic components such as p-methoxycinnamic acid, N,N-dimethyl-p-aminobenzoic acid, and inorganic components such as silicon oxide with diameters up to 1 micrometer, and have advantageous properties as mixtures containing these particles in concentration of 30 wt % do not develop white appearance. Petrolatum containing 10 wt % of only these particles have SPF (sun protection factor) of 13 proving that these particles are very effective in blocking UV rays. However, as p-methoxycinnamic acid and N,N-dimethyl-p-aminobenzoic acid absorb UV B with lambda max at 290 nm, their UV A blocking efficacy is still low as they remove only a small amount of UV A by scattering.

Currently available UV A ingredients such as Avobenzone, Benzophenone 3 are absorbed into human body and contain highly photo-reactive benzophenone group. Benzophenone group is concerned with it safety and consumer organizations are demanding to ban these compounds. For Avobenzone, their photoreaction products are also concerned for their toxicity.

On the other hand, an organic sun blocking agent, Tinosorb S, the chemical name of which is 2,2'-[6-(4-methoxyphenyl)-1,3,5-triazine-2,4-diyl-]bis{5-2(ethylhexyl)oxy}phenol} absorbs both UV A and UV B rays and has low possibility of skin penetration because its molecular weight is high. But Tinosorb S has very low solubility in water and organic solvents, consequently, it is often used in solid form. Their melting temperature is 70-80° C. that is relatively higher than other organic compounds and they can easily undergo phase separation to turn into viscous insoluble liquid and form aggregates in cosmetics causing difficulty in formulating. Also, it has problems related to yellow color and unpleasant odor.

Accordingly, development of UV ingredients that absorb both UVA and UVB, do not penetrate skin, can be easily removed from skin after use, have no aesthetic issues, and are easy to use in cosmetics formulation are highly demanded.

The Korean Patent 1206939 describes a method for preparation of poly(organosilicon oxide) particles of polysilsesquioxane containing UV chromophores selected from a groups of silsesquioxane-siloxane hybrid polymers, silsesquixoxane-silica hybrid polymers, silsesquioxane-siloxane-silica hybrid polymers, and silsesquioxane-siloxane hybrid polymers including steps of polymerizing organoalkoxysilane precursors selected from organotrialkoxysilane, diorganodialkoxysilane containing UV chromophores, and mixture thereof, and silanes, serving as crosslinking controller and UV stability enhancer, selected from a groups of tetraalkoxysilane, alkyltrialkoxysilanem tetraalkoxysilane, aryltrialkoxysilane, dialkyldialkoxysilane, diaryldialkoxysilane, arylalkyldialkoxysilane, and mixtures thereof. The silicone powders described in the cited patent are very different from powders of the present invention in that they absorb only UV B.

[Throughout the specification, a number of publications and patent documents are referred to and cited. The disclosures of the cited publications and patent documents is incorporated herein by reference in its entirety to more clearly describe the state of the related art and the present disclosure.

DETAILED DESCRIPTION OF THE PRESENT INVENTION

Objectives

The inventors of the present invention have made efforts to prepare poly(organosilicon oxide)s that are impermeable to skin as they are non-nano sized particles or have molecular weight higher than 500, and contain chromophores that do not produce radicals easily, unlike benzophenone. As a result, they have developed high molecular weight polysilsesquioxanes that absorb not only UV B as they contain UV B chromophore but also UV A by inducing chromophores to be located close enough in particles to form excimers or exciplexes.

The objective of the present invention is preparing noble UV blocking materials that absorb both UV A and UV B without containing UV A chromophores that are known to be harmful to human health such as benzophone homologues.

Accordingly, the present invention is directed to providing polysilsesquioxanes that are useful as UV blocking agent or UV booster that are safe and easily applicable to cosmetics formulation processes as they do not intrude into human body because they have sizes larger than 100 nm and high molecular weights, do not develop opaque white appearance even when added in high concentrations (30%), and have good sensory.

Other objects and advantages of the present invention will become apparent from the detailed description to follow taken in conjunction with the appended claims and drawings.

Solution to the Problem

In one aspect, the present invention provides crosslinked polysilsesquioxane random copolymers with new properties of absorbing UV B that the chromophore in the polymer originally absorbs and additionally UV A by driving chromophores to form excimers or exciplexes in the polymers including polysilsesquioxane Monomer 1 containing UV B chromophores and silane Monomer 2 serving as microstructure controller.

As used herein, the term "chromophore" refers chemical groups that absorb light to develop colors. Most of chromophores contain unsaturated bonds and π electrons in unsaturated bonds are excited by absorbing light. More recently, chromophores mean atoms and atomic groups that absorb light including ultraviolet rays.

As used herein, the term "silane compounds" refers to chemical compounds containing silane (Si) atom that can be expressed $SiR_4$ (R is any chemical group that can be bound covalently to Si such as hydrogen, alkyl, alkoxy, amide groups), more specifically, silane compounds are precursors of silsesquioxane, siloxane, silica and combination of them, but is not limited thereto.

As used herein, the term "microstructure controller" refers to any material that is used to control micro structures of the polymers including arrangement of chromophores in appropriate positions where they can form excimers and exciplexes in the poly(organosiloxane)s produced from chromophore containing monomers described above and further forcing chromophores to get closer to expand the UV absorbing range. The microstructure controllers allow manipulating photophysical properties, physical and mechanical properties, and morphologies of the final products by affecting the crosslinking density and positions and spatial distances between chromophores depending on co-polymerizing method and amounts used.

As used herein, the term "excimer" or "exciplex" refers complex formed between two or more chromophores that are physically located at appropriate locations that absorb new (longer) wavelengths. Excimers are formed between identical chromophores while exciplexes are formed between different chromophores. These phenomena are observed especially when close-by aromatic chromophores are overlapped. The wavelengths that excimers or exciplexes absorb have longer wavelengths than the wavelengths that chromophores originally absorb and the difference depends on the nature of interactions between chromophores, the chromophores structure, spatial distances between chromophores, and degree of overlapping. Following the theoretical background of excimer and exciplex, materials that absorb new spectrum of wavelengths can be prepared by placing chromophores in appropriate positions for excimer and exciplex formation.

As used herein, the term "random copolymers" refers to polymers where two or more monomers are combined without any regular sequence that is different from alternating copolymers where two or more monomers are alternatively bound one after another. The composition of monomer A and monomer B in the random copolymers are not necessarily the same as the composition of monomer A and monomer B used to prepare the random copolymers.

As used herein, the term "cross-linked random copolymer" refers to random copolymers that have cross-linked or network structures by chemical bonds. The chemical bonds are either intramolecular bonds between chemical groups within a single polymer molecule or intermolecular bonds between chemical groups in different polymer molecules. Cross-linked random copolymers have more compacted structure due to the cross-linked or network structure produced by chemical bonds described above.

The chromophores used in crosslinked polysilsesquioxane random copolymers in the present invention are mostly bulky chemical groups containing benzene ring. Bulky chromophores in precursors make polymerization difficult and even if they are polymerized, bulky chromophores repel each other by steric repulsion and are located far separated from each other. Separated far, chromophores in polymers prepared from only monomers containing chromophores do not form excimer or exciplexes and polymers absorb the lights of the same wavelengths that original chromophores absorb. If polymers are prepared from precursor or monomer containing chromophores and co-monomers following the method described in Korean Patent 1206939, monomers containing chromophores and co-monomer react discriminately as they have different reactivity to form block copolymers consisting of blocks of ambient number of units from the co-monomer and units from the monomer containing chromophore. Chromophores in copolymers are separated like in homopolymers and excimers or exciplexes do not form. As a result, co-polymerization gives polymeric particles that absorb only lights that the chromophore originally absorbs.

Contrastingly, the present invention provides polymers that contain only UV B chromophores but absorb both UV A and UV B by providing appropriate spaces between chromophores in polymers in different methods including pretreatment of monomers containing bulky chromophores, temperature control, and employment of microstructure controlling co-monomers that allow chromophores located at appropriate positions to form exciplexes or excimers. The remaining silanol (SiOH) groups are further reacted by heating to increase the density of crosslinking, that further stabilizes excimer and exciplex conformations to obtain polysilsesquioxane polymers with consistent UV absorbing properties even after being exposed to heat and solvents.

In accordance with the present invention, the role of microstructure controllers in formation of excimers and exciplexes are apparent, as described in Examples, from the fact that polymeric powders prepared from only monomers containing chromophores, powders prepared from mixtures of UV B monomers containing chromophores and co-monomers by the method described in Korea Patent 1206939, and powders obtained from mixtures of UV B monomer and phenyltrimethoxysilane, a silane containing bulky group, as a trial microstructure controller absorb only UV B that incorporated. UV B chromophores absorb while polymeric powders prepared from the same mixtures by the method described in the present invention absorb UV A in addition to UV B that chromophores involved originally absorb.

FIG. 1a shows that chromophores (represented as rectangles) in polymers prepared from only monomers containing chromophores are located far from each other so that excimer or exciplex cannot form while chromophores in crosslinked polymers prepared from monomers containing chromophores and microstructure controller are located closer.

FIG. 1b shows that heating the polymers increases the density of crosslinking as the microstructure controller reacts further so that chromophores get closer each other. The energy minimized model structures of dimer (FIG. 1c) and tetramer (FIG. 1d) of 3-aminoproplytrimethoxysilane bound to p-methoxycinnamoyl group show that chromophores are in the opposite sides while p-methoxycinnamoyl groups are located closer in tetramer containing silica as microstructure controller (FIG. 1e). As described above, it is very important to prevent formation of such as block copolymers from mixtures of precursors containing chromophore and microstructure controller.

In one aspect, the present invention provides crosslinked polysilsesquioxane random copolymers that absorb both UV A and UV B as a result of excimer or exciplex formation between chromophores involving (i) polysilsesquioxane Monomer 1 containing chromophores selected from a group consisting of molecules with chemical structures 1 to 3 shown below or mixtures thereof and (ii) Monomer 2 serving as microstructure controller selected from a group consisting of tetraalkoxysilane, alkyltrialkoxysilane, aminoalkyltrialkoxysilane, aryltrialkoxysilane dialkyldialkoxysilane, diaryldialkoxysilane, arylakyldialkoxysilane and mixtures thereof.

<Chemical Structure 1>

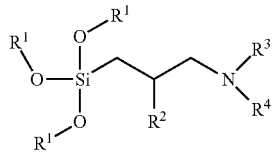

<Chemical Structure 2>

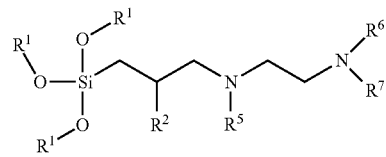

<Chemical Structure 3>

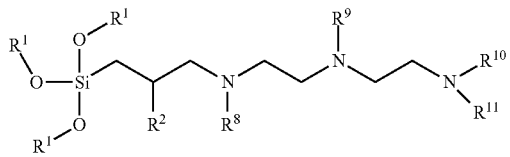

In chemical structures above. $R^1$ is independently a $C_1$-$C_{10}$ alkyl group, $R^2$ is hydrogen or a $C_1$-$C_{10}$ alkyl group, $R^3$-$R^4$ in chemical structure 1, $R^5$-$R^7$ in chemical structure 2, $R^8$-$R^{11}$ in chemical structure 3 are independently (a) hydrogen or (b) a chromophore absorbing only UV B.

The chromophore used in the present invention may be any UV-absorbing group known in the art. Specifically, at least one of $R^3$ and $R^4$ in chemical structure 1, at least one of $R^5$ to $R^7$ in chemical structure 2, and at least one of $R^8$ to $R^{11}$ in chemical structure 3 may be chemical groups selected from a group of cinnamoyl group or and alkoxy derivatives thereof, benzoyl group or dialkylamino cinnamoyl group, benzylidene camphor sulfonyl group, salicyloyl group, acetyl salicyloyl group, and coumarin carboxy group, but is not limited thereto.

In an exemplary embodiment of the present invention, at least one of $R^3$ and $R^4$ in chemical structure 1, at least one of $R^5$ to $R^7$ in chemical structure 2, and at least one of $R^8$ to $R^{11}$ in chemical structure 3 may be chromophores selected from a group of cinnamoyl group, cinnamoyl groups substituted with alkoxy, benzoyl group, benzyl group substituted with alkylcarboxyl group, benzylidene camphor sulfonyl group, salicyloyl group, or coumarin carboxy group, more specifically p-methoxycinnamoyl group, p-N,N-dimethylbenzoyl group, or o-acetylsalicyloyl group shown below in chemical structures 4 to 5, but is not limited thereto.

<Chemical Structure 4>

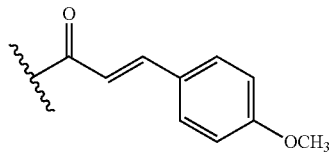

<Chemical Structure 5>

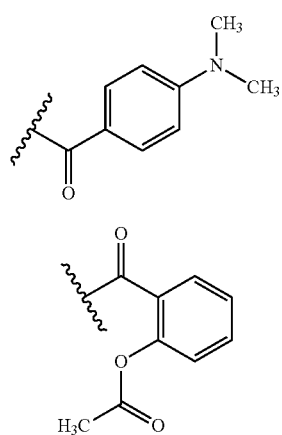

<Chemical Structure 6>

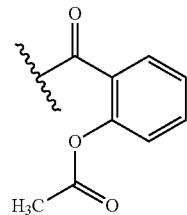

In an exemplary embodiment of the present invention, when one of $R^3$ and $R^4$ in chemical structure 1, one of $R^6$ and $R^7$ in chemical structure 2, and one of $R^{10}$ and $R^{11}$ in chemical structure 3 is a chromophore selected from a group of cinnamoyl, alkoxy derivatives of cinnamoyl, benzoyl, alkylcarboxyl derivatives of benzoyl, benzylidene camphor sulfonyl, salicyloyl, and coumarin carboxyl groups, the other R group may be hydrogen, but is not limited thereto.

In an exemplary embodiment of the present invention, in crosslinked random polysilsesquioxane copolymers in the present invention (ii) microstructure controller is specifically a silane compound selected from a group of tetraalkoxysilane, alkyltrialkoxysilane, aminoalkyltrialkoxysilane, aryltrialkoxysilane, dialkyldialkoxysilane, diaryldialkoxysilane, arylalkyltrialkoxysilane, and mixtures of thereof, but is not limited thereto.

In an exemplary embodiment of the present invention, tetraalkoxysilane may be tetraalkoxysilane containing $C_1$-$C_{10}$ alkoxy group, more specifically tetramethoxysilane, tetraethoxysilane, tetrakis[2-(2-methoxyethoxy)ethoxy]silane or tetrakis(methoxethoxy)silane, but is not limited thereto.

In an exemplary embodiment of the present invention, alkyltrialkoxysilane may be alkyltrialkoxysilanes containing $C_1$-$C_{10}$ alkyl and $C_1$-$C_{10}$ alkoxy groups, more specifically propyltrimethoxysilane, ethyltrimethoxysilane, methyltrimethoxysilane, propyltriethoxysilane, ethyltriethoxysilane or methyltriethoxysilane, but is not limited thereto. In an exemplary embodiment of the present invention, aminoalkyltrialkoxysilane may be aminoalkyltrialkoxysilane containing $C_1$-$C_{10}$ alkyl and $C_1$-$C_{10}$ alkoxy groups, more specifically aminomethyltrimethoxysilane, aminopropyltrimethoxysilane, or aminopropyltriethoxysilane, but not limited thereto.

In an exemplary embodiment of the present invention, aryltrialkoxysilane may be aryltrialkoxysilanes containing $C_6$-$C_{10}$ aryl groups and $C_1$-$C_{10}$ alkoxy groups, more specifically naphtyltrimethoxysilane, phenyltrimethoxysilane, or phenyltriethoxysilane, but not limited thereto.

In an exemplary embodiment of the present invention, dialkyldialkoxysilanes may be dialkyldialkoxysilanes containing $C_1$-$C_{10}$ alkyl groups and $C_1$-$C_{10}$ alkoxysilanes, more specifically propylmethyldimethoxysilane, ethylmethyldimethoxysilane, dimethyldimethoxysilane, methylpropyldiethoxysilane, diethyldiethoxysilane or dimethyldiethoxysilane, but is not limited thereto.

In an exemplary embodiment of the present invention, diaryldialkoxysilanes are diaryldialkoxysilane containing $C_6$-$C_{10}$ aryl groups and $C_1$-$C_{10}$ alkoxy groups, more specifically diphenyldimethoxysilane or diphenyldiethoxysilane, but not limited thereto.

In an exemplary embodiment of the present invention, arylalkyldialkoxysilanes are aryldialkoxysilane containing $C_6$-$C_{10}$ aryl groups, $C_1$-$C_{10}$ alkyl groups, and $C_1$-$C_{10}$ alkoxy groups, more specifically phenylmethyldimethoxysilane, phenylmethyldiethoxysilane, phenylethyldimethoxysilane, or phenylethyldiethoxysilane, but not limited thereto.

One of the most important features of the present invention is tetraalkoxysilane, alkyltrialkoxysilane, aryltrialkoxysilane, dialkyldialkoxysilane, diaryldialkoxysilane, and arylaklyldialkoxysilane serving as microstructure controller lead chromophores in polysilsesquioxanes to have appropriate arrangement and fix them so that polysilsesquioxanes absorb additional UV rays that chromophores involved originally do not absorb. In an exemplary embodiment of the present invention, when only silsesquioxane monomer containing p-methoxycinnamic acid as chromophore is polymerized in conventional method, the resulting polysilsesquioxane absorbs UV B, 280-320 nm, with lambda max at 290 nm that p-methoxycinnamic acid originally absorbs, but when the same UV B absorbing monomer and tetraalkoxysilane, aryltrialkoxysilane, and alkyltrialkoxysilane are polymerized in well controlled method that leads to formation of random copolymers instead of block copolymers, the p-methoxycinnamoyl group in the copolymers form excimers and the resulting polymers absorb UV A of 320-400 nm in addition to UV B of 28-320 nm. The physical properties of polymers can be customized by adjusting the nature of microstructure controller, amounts of microstructure controller, and reaction conditions, especially when particles are prepared, the sizes can be customized. Applying the principles described above allows preparation of extraordinary UV blocking ingredients that are not absorbed, non-nano sized, and block UV B and UV A simultaneously although they contain UV B chromophores that are superior to UV A ingredients containing hazardous benzophenone groups, nano sized titanium dioxide and zinc oxide with concerns of hazardous effects of too small sizes and various aesthetical issues. Tetraalkoxysilane, alkyltrialkoxysilane, aminotrialkoxysilane, aryltrialkoxysilane, arylaklydialkoxysilane, dialkyldialkoxysilane, and diphenyldialkoxysilanes used as microstructure controllers in this present invention also function as excellent suppressing agents of white appearance development.

The crosslinked polysilsesquioxane random copolymers in the present invention are hybrids of organic components such as p-methoxycinnamic acid or N,N-dimethyl-p-aminobenzoic acid and inorganic components such as silsesquioxane with large diameters with superior aesthetic properties as sunscreens that contain them in 30 wt % do not develop white appearance, and have good UV blocking efficacy as sunscreens containing 10 wt. % of them have sun protection factor (SPF) value of 13.

The crosslinked polysilsesquioxane random copolymers in the present invention have good lubricating properties and spread on the skin smooth with good sensory when used in cosmetics.

The weight ratio between (i) Monomer 1 containing chromophore and (ii) crosslinking Monomer 2 is not be limited to any specific range, for example it may be between 100:1 to 1:5.

In one aspect, the present invention provides a method for preparing crosslinked polysilsesquioxane random copolymers with a new feature of absorbing UV A in addition to UV B that the chromophore involved originally absorbs as excimers or exciplexes are formed in the polymers including steps of (a) dissolving (i) silsesquioxane Monomer 1 containing chromophores and (ii) Monomer 2 serving as microstructure controller in solvents separately; and (b) polymerizing Monomer 1 and Monomer 2 to obtain crosslinked polysilsesquioxane random copolymers where excimers and exciplexes are formed to absorb wavelengths (UV A) in addition to those chromophores incorporated into the polymer originally absorb (UV B) including mixing solutions of Monomer 1 and Monomer 2.

In one aspect, the present invention provides a method for preparing crosslinked polysilsesquioxane random copolymers that includes (a) a step separately dissolving (i) silsesquioxane Monomer 1 selected from a group consisting of chemicals with structures shown in Chemical Structures 1 to 3 shown below and (ii) Monomer 2 serving as microstructure controller selected from a group consisting of tetraalkoxysilane, alkyltrialkoxysilane, aminoalkyltrialkoxysilane, aryltrialkoxysilane, dialkyldialkoxysilane, diaryldialkoxysilane, arylalkyldialkoxysilanes or mixtures of them; and (b) a step mixing the Monomer 1 silsesquioxane monomer solution and the Monomer 2 solution to have them react.

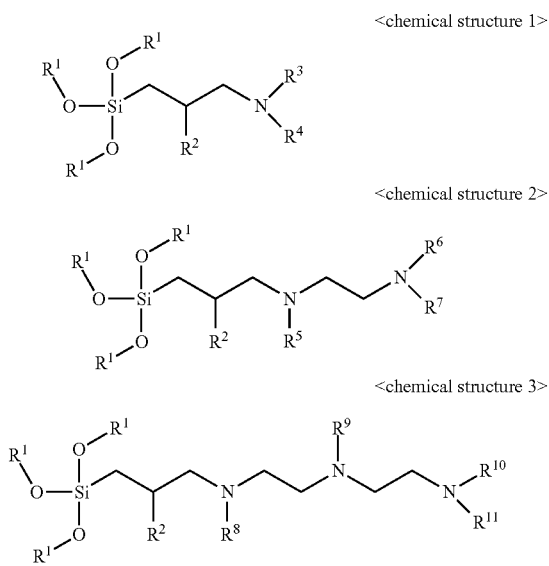

<chemical structure 1>

<chemical structure 2>

<chemical structure 3>

$R^1$ in the chemical structure above may be independently $C_1$-$C_{10}$ alkyl group, $R^2$ may be hydrogen or $C_1$-$C_{10}$ alkyl group, $R^3$-$R^4$ in chemical structure 1, $R^5$-$R^7$ in chemical structure 2, and $R^8$-$R^{11}$ in chemical structure 3 may be independently (a) hydrogen or (b) a UV B absorbing chromophore selected from a group consisting of cinnamoyl group, cinnamoyl group substituted with alkoxy group, benzoyl group, benzoyl group substituted with alkylcarboxyl group, benzylidene camphor sulfonyl group, salicyloyl group, and coumarin carboxyl group, but not limited thereto.

In another exemplary embodiment of the present invention, the present invention provides crosslinked polysilsesquioxane random copolymers that are prepared following the method described above.

Since crosslinked polysilsesquioxane random copolymers prepared in this method and the crosslinked polysilsesquioxane random copolymers described earlier in the present invention include identical crosslinked polysilsesquioxane random copolymers, Monomer 1 containing chromophores, microstructure controllers, and related processes, common descriptions are omitted in order to avoid complexity of the specifications.

Polysilsesquioxane random copolymers prepared in the method described in the present invention have similar overall compositions to organosilicon oxide polymers described in Korean Patent 1206939, however they have very different photo-chemical properties because they have different repeat unit sequences or micro-structures. Since reactivity of the monomers containing chromophores are very different from that of co-monomers, repeating units in copolymers are distributed in such a way that chromophores cannot get close to interact each other. In the polymerization method of the present invention, obtained poly(organo silicone oxide)s have new photo-chemical properties and physical properties as silsesquioxane monomers containing chromophores and co-monomers (microstructure controller hereafter) are independently pre-treated by chemical methods before co-polymerization, considering their different reactivity, to induce repeat unit distributions in polymers that allow formation of excimers or exciplexes.

In an exemplary embodiment of the present invention, the solvent in step (a) described above may be independently selected from a group consisting of alcohols such as methanol, ethanol, isopropanol, and butanol; alcohols with ether such as ethylenegylcolethyl ether, propyleneglycolethyl ether; ethers such as diethyl ether, tetrahydrofuran, dioxane; ketones such as acetone methylethylketone; water and mixtures of them, but not limited thereto.

[In an exemplary embodiment of the present invention, the pH of the solvent in step (a) may be adjusted to acidic conditions (pH lower than 7) prior to use.

In an exemplary embodiment of the present invention, the reaction by mixing in step (b) may be performed at basic conditions (pH higher than 7).

The acid used to adjust the pH of the solvent in step (a) described above may be any acid known in the art (for example inorganic acid such as hydrochloric acid and organic acid such as acetic acid). Specifically, the acids may be hydrochloric acid (HCl), sulfuric acid ($H_2SO4$), and more specifically hydrochloric acid (HCl).

[The base used to adjust the pH of the solvent in step (b) describe above may be any base known in the art (for example, organic base such as amine and inorganic base such as sodium hydroxide). Specifically, the bases may be NaOH, KOH, $Ca(OH)_2$, $Ba(OH)_2$, CsOH, $Sr(OH)_2$, LiOH, RbOH, $Mg(OH)_2$, triethylamine, and ammonia, more specifically, NaOH or KOH, the most specifically NaOH.

In an exemplary embodiment of the present invention, the process may include step (c) where the products from step (b) are heated. Heating may be performed to maintain the temperature between 15° C. and 99° C., but not limited hereto.

In an exemplary embodiment of the present invention, the process may include step (d) where the heated products from step (c) are cooled to room temperature. The room temperature means the arbitrary atmosphere temperature, commonly 1-35° C., specifically 15-25° C., but not limited hereto. The cooling process may be performed by any method applicable to cooling in the art such as storing at room temperature, and storing in refrigerator.

In an exemplary embodiment of the present invention, the preparation may include step (e) where the pH of the products from step (d) are adjusted to 5-8. The pH is adjusted using any acid or base described in steps (a) and (b) described above. pH adjusting step (e) is not necessary when the pH of the products from step (d) is within 5-8.

In an exemplary embodiment of the present invention, the preparation process may include steps to recover and dry the products. Recovery of the products may be performed using any method used to separate solid materials from liquids such as centrifugation and filtration, and drying may be performed using any method used to remove residual liquids from the products such as natural drying at room temperature, heating, drying under vacuum, and freeze drying.

In an exemplary embodiment of the present invention, the preparation method includes steps of pretreating silsesquioxane precursor and microstructure controller independently in acidic conditions, followed by mixing them to react, and heating and cooling the reaction mixture. This method has been developed to induce non discriminated reactions between silsesquioxane precursors and microstructure controllers of different reactivity so that excimers and exciplexes are formed in the polymer to obtain polymers that have completely different photophysical properties from polymers prepared by direct reaction of silsesquioxane precursor and microstructure controller.

Following the method in the present invention, diameters of pol(organosilicon oxide)s may be controlled from tens of nanometers to a few nanometers, the sensory and surface properties may be customized by adjusting the relative amounts of silsesquioxane precursor and crosslinking controller, amounts of solvent (for example, water), reaction time, amount of base. Specifically, the diameters of polysilsesquioxane powders prepare in the present invention are hundreds of nanometers.

The inventors of the present invention have made efforts to prepare poly(organosilicon oxide) that absorb both UV A (320-400 nm) and UV B (280-320 nm) effectively with molecular weights high enough not to penetrate skin that are especially applicable to sunscreens to protect skin. As a result, they have found that they can prepare poly(organosilicon oxide) that absorb both UV A and UV B as a result of excimer or exciplex formation when (i) silsesquioxane precursor containing UV B absorbing chromophore and (ii) as microstructure controller, tetraalkoxysilane, alkyltrialkoxysilane, aryltrialkoxysilane, dialkyldialkoxysilane, diaryldialkoxysilane, arylalkyldialkoxysilane or mixture of them are appropriately reacted in the presence of base and acid. Furthermore, they have found that properties of resulting polysilsesquioxane random copolymers can be customized by controlling the relative amounts of silsesquioxane precursors and microstructure controller in polymerization, and that the light absorbing properties of the products do not change even after heating at 100-150° C. for longer than 10 hours or keeping them in solvents such as ethanol for a long period of time. The inventors of the present invention proved that polysilsesquioxanes prepared in the present invention have new microstructures by confirming that polysilsesquioxanes prepared solely from silsesquioxane precursor containing UV chromophore without using appropriate microstructure controller, and polysilsesquioxanes prepared using microstructure controllers in inappropriate method do not absorb new wavelengths because no exciplexes or excimers are formed.

The crosslinked polysilsesquioxane random copolymers containing chromophores may be applied to blocking UV and other purposes where their fluorescent properties may be applicable. More specifically, they may be used as UV protecting agent in UV blocking cosmetics, bioscience products, fibers, rubbers, paper, leathers, plastics, foods and cosmetics for sunscreens with enhanced safety.

Effects of the Invention

The features and advantages of the present invention are summarized as follows.

The present invention provides crosslinked polysilsesquioxane random copolymers and method to prepare the same, including polysilsesquioxane Monomer 1 containing chromophore and silane Monomer 2 as microstructure controller, that absorb UV A in addition to UV B that chromophores in the Monomer 1 originally absorbs as a result of excimer or exciplex formation between chromophores in polymers.

The crosslinked polysilsesquioxane random copolymers prepared in the present invention provides excellent sensory, and are safe as they are not absorbed through skin into human body because of high molecular weights. Also, they have excellent UV blocking ability as they absorb not only UV B (280-320 nm) but UV A (320-400 nm) as a result of excimer or exciplex formation between chromophores, and can be applied in formulating sunscreens as mixtures containing 30% of them did not develop white appearance.

BRIEF DESCRIPTION OF THE DRAWINGS

FIG. 1c shows chromophores are located in opposite sides to have no interactions and FIG. 1d shows chromophores are still separated too far to interact each other while FIG. 1d shows chromophores get closer when $Si(OH)_4$ is inserted as microstructure controller.

DETAILED DESCRIPTION OF THE INVENTION

The present invention will now be described in further details by examples. It would be obvious to those skilled in the art that that these examples are intended to be more concretely illustrative and the scope of the present invention as set forth in the appended claims is not limited to or by the examples.

EXAMPLES

Throughout the specification, "%" used to indicate concentrations of specific compounds is weight/weight % for solid/solid, weight/volume % for solid/liquid, and volume/volume % for liquid/liquid unless mentioned otherwise.

Example 1: Preparation of trimethoxysilylpropyl-p-methoxycinnamide

To a solution of 100 p-methoxycinnamic acid (Sigma-Aldrich Co.) dissolved in 500 mL of toluene, 100 mL of thionyl chloride (Oriental Steel Chemicals Co.) was added slowly. The reaction mixture was cooled to room temperature after refluxing for 18 hours, the reaction mixture was purged with nitrogen gas for 3 hours. Eighty grams of triethylamine (Sigma-Aldrich Co.) and 110 g of 3-aminopropyltrimethoxysilane (Sigma-Aldrich Co.) was mixed slowly. The reaction mixture was agitated for 5 hours at 60° C. and then cooled to room temperature. The salt was removed by vacuum filtration and toluene was removed under vacuum to obtain trimethoxysilylpropyl-p-methoxycinnamide (I). The purity of obtained precursor was checked using silica thin layer chromatography.

Example 2: Preparation of poly(organosilicon oxide) from trimethoxysilylpropyl-p-methoxycinnamide (Comparison Compound 1)

Figure 1A:
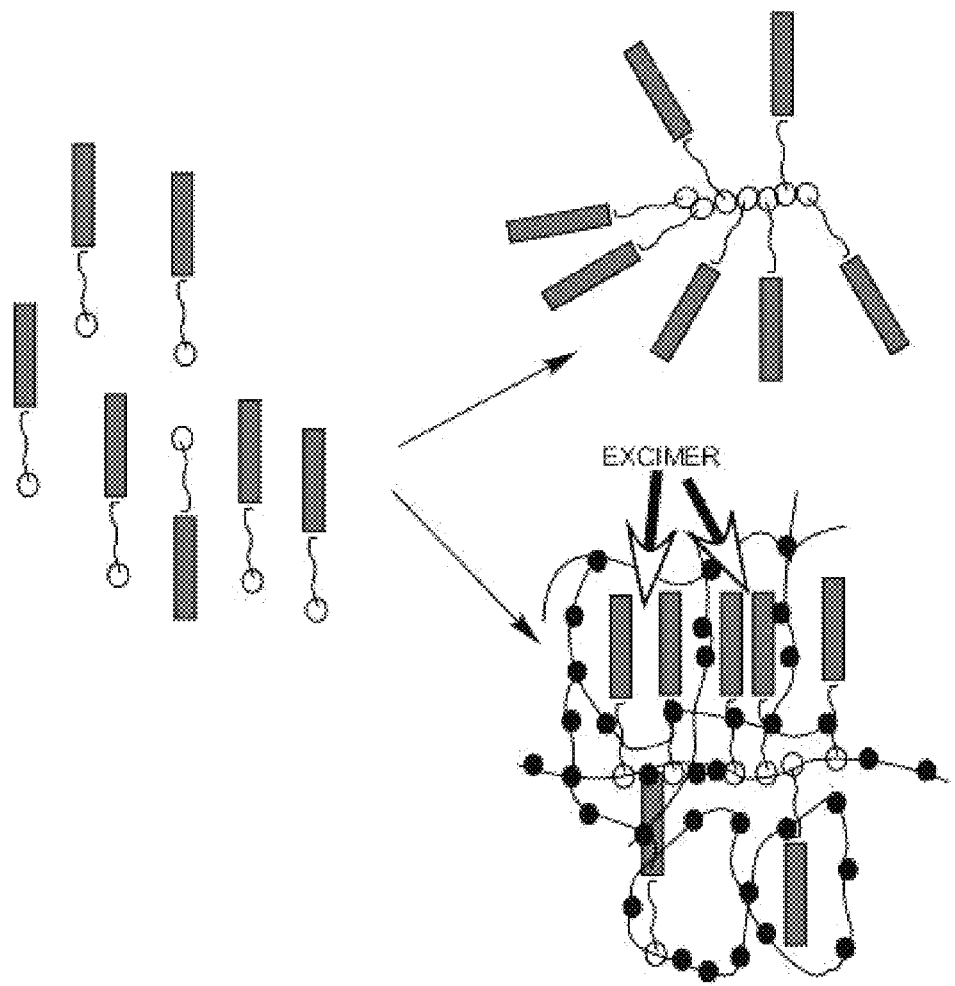
FIG. 1a illustrates formation of excimers/exciplexes. Polymerization of only molecules containing chromophores indicated as rectangle results in separation of chromophores so that excimers/exciplexes do not form but co-polymerization with microstructure controller allows chromophores get closer and excimers/exciplexes can form.
Figure 1B:
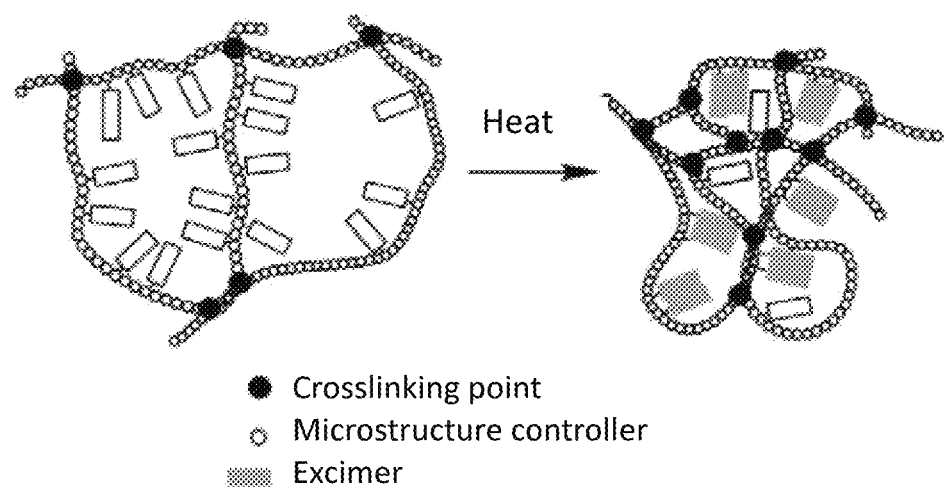
FIG. 1b illustrates the effect of heating. Heating increases crosslinking density forcing chromophores to get closer and the polymers becomes more stable to further heating or solvent exposure.
Figure 1C:
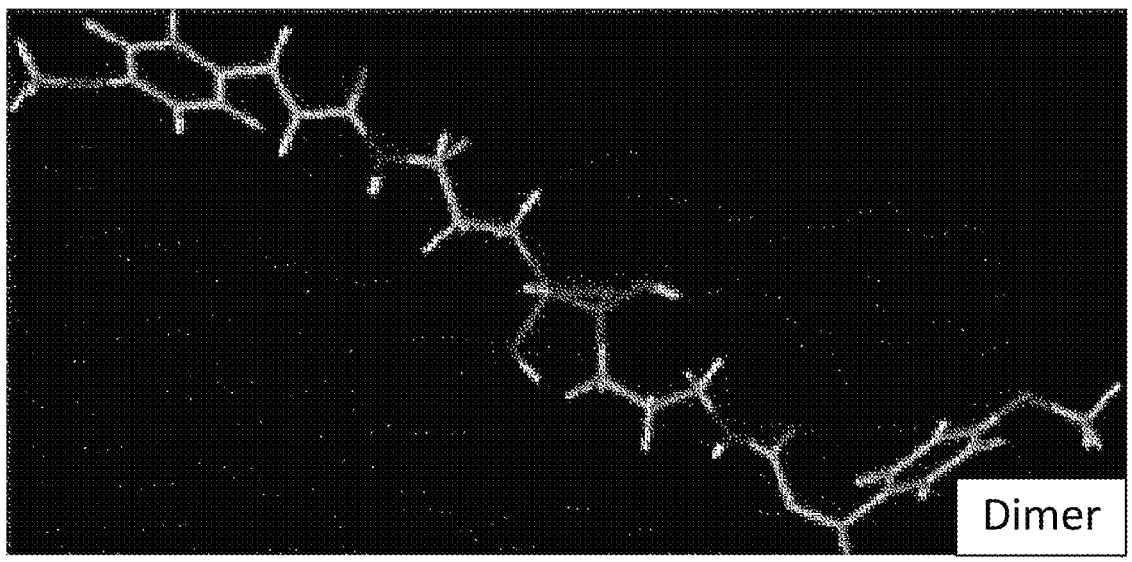
FIG. 1c to 1e show computer simulated most stable configurations for dimer (FIG. 1c) and tetramer (FIG. 1d) of 3-inopropyltrimethoxysilane containing p-methoxycinnamic acid as chromophore, and tetramer (FIG. 1e) where silica is bound between silicone repeat units containing chromophore as microstructure controller.
Figure 1D:
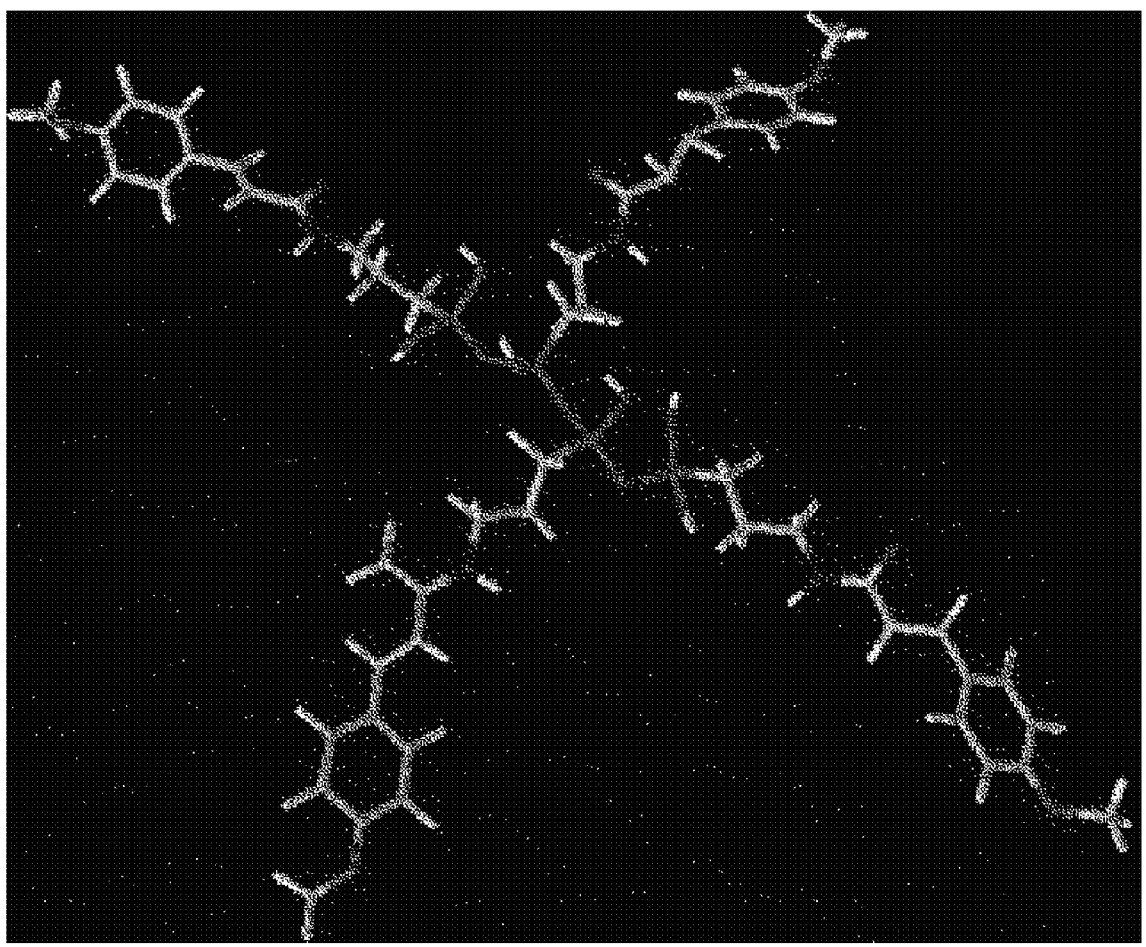
Figure 1E:
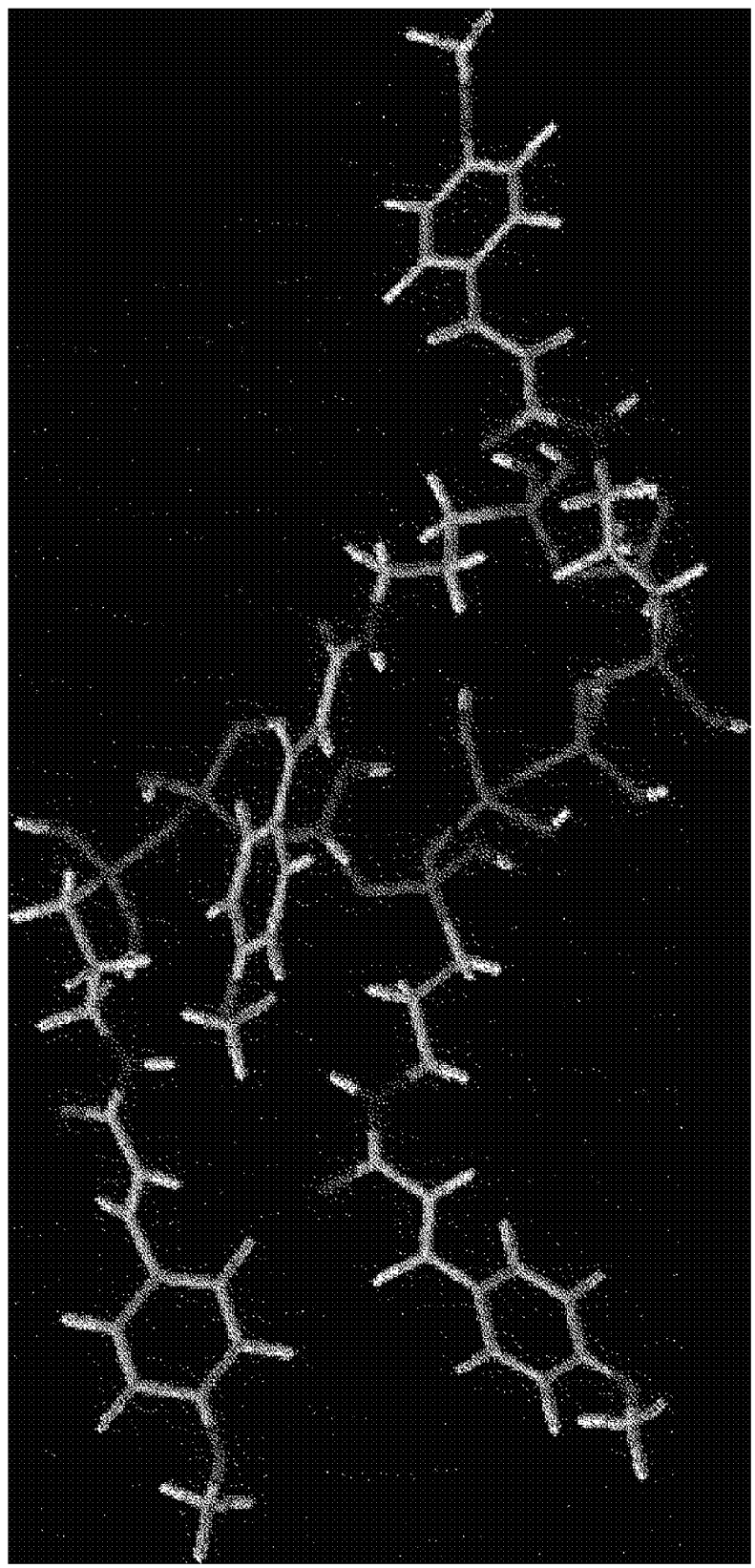
Figure 2A:
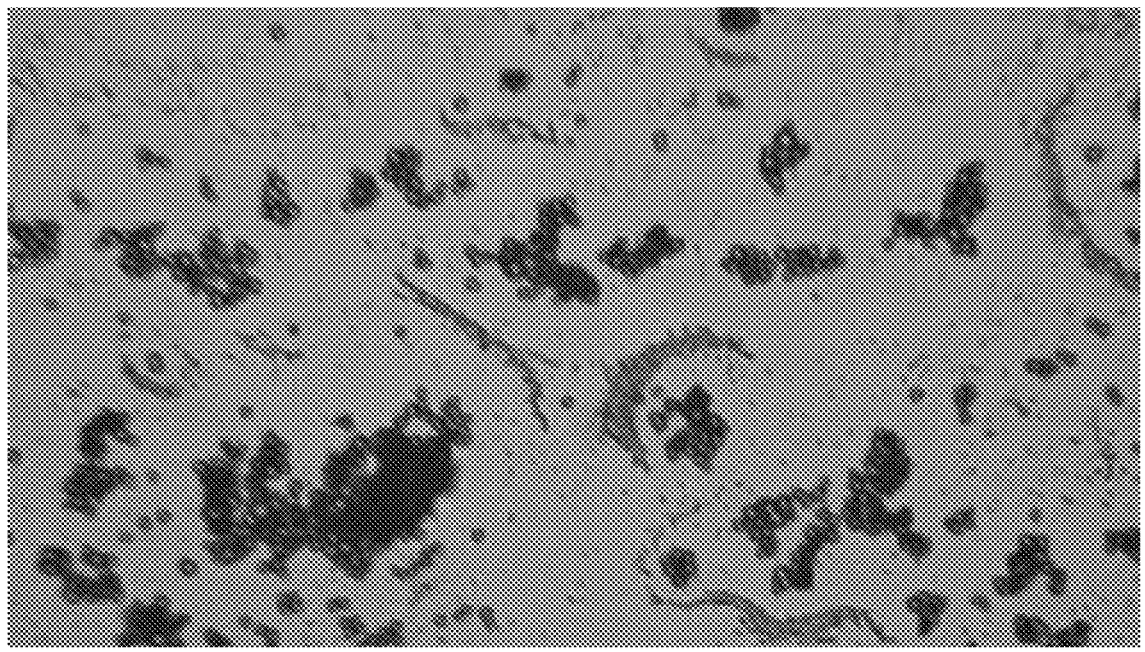
FIG. 2a shows a SEM image of particles prepared in Example 2.
Figure 3:
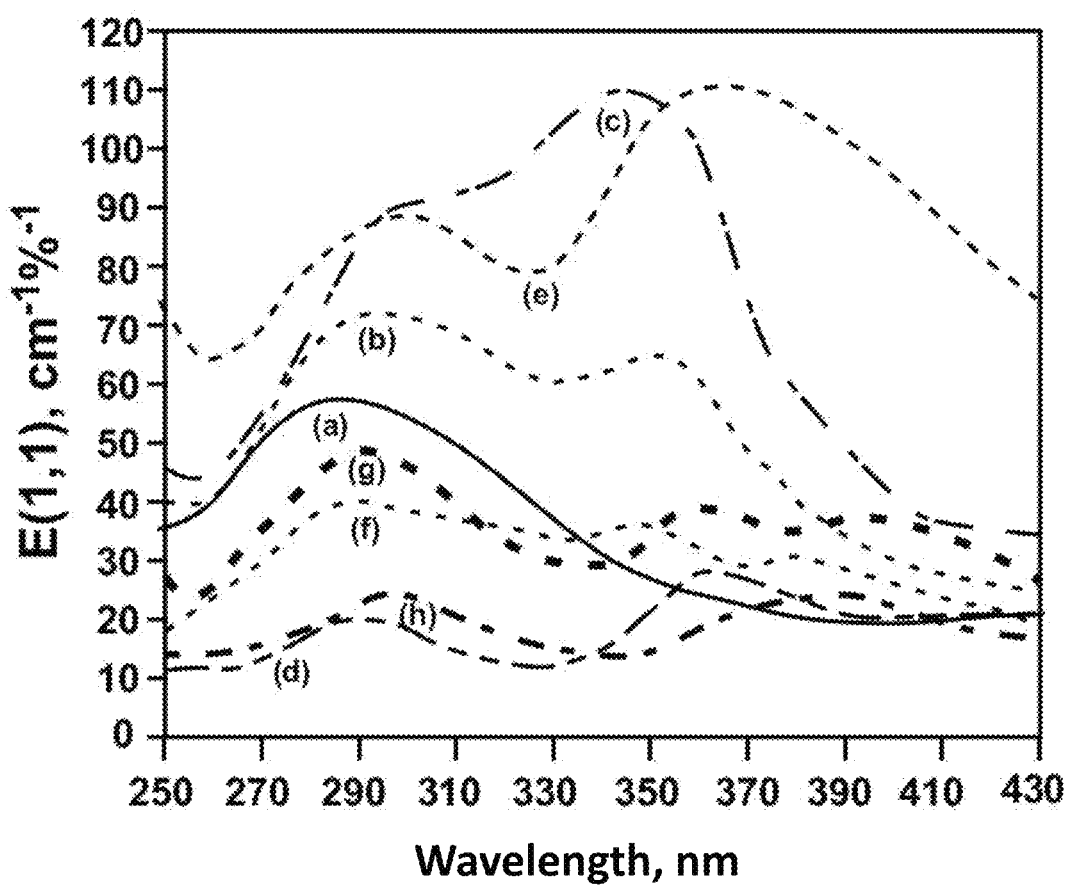
FIG. 3 shows UV/Vis absorption spectra of powders prepared in Examples 2, 4, 5, 7, 10, 12, 14, 16.

One hundred grams of trimethoxysilylpropyl-p-methoxycinnamide prepared in example 1 was heated to melt and then added slowly to 5 L water at 20° C. while being agitated vigorously. To the colloid solution, 30 mL of 10% NaOH aqueous solution was added and the mixture was agitated vigorously for 18 hours. The pH of the mixture was adjusted using 10% HCl solution and filtered to recover the solid products. The obtained solid products was slightly soluble in ethanol or methanol, and the insoluble solid products had spherical shape. Observation by optical microscopy showed that the powders had about 2 micrometers diameters (FIG. 2a), with lambda max at 290 nm and E(1,1) of 57 $cm^{-1}\%^{-1}$ (Spectrum a in FIG. 3).

Example 3: Preparation of poly(organosilicon oxide) from trimethoxysilylpropyl-p-methoxycinnamide and methyltrimethoxysilane Fifty grams of trimethoxysilylpropyl-p-methoxycinnamide and 50 g of methyltrimethoxysilane were dissolved in 200 mL of ethanol and added to 4 L of water to obtain an emulsion, followed by immediate adjustment of pH to 10 using 10% NaOH solution. The mixture was agitated for 18 hours at room temperature and the pH was adjusted to 7 using dilute HCl solution. Insoluble particles were recovered by centrifugation and washed with 500 mL water and 200 mL ethanol followed by drying at 120° C. until the weight did not change. The powder was crushed and sieved to obtain about 20 g of fine powders. The diameters of particles were about 1 micrometer and gave virtually identical UV/Vis spectrum to that of particles obtained in example 2. The E(1,1) value of the product was 110 $cm^{-1}\%^{-1}$.

Example 4: Preparation of polysilsesquioxane random copolymer from trimethoxysilylpropyl-p-methoxycinnamide and methyltrimethoxysilane (particles absorbing both UV A and UV B)

Fifty grams of trimethoxysilylpropyl-p-methoxycinnamide prepared in example 1 was dispersed in 100 mL of 50% aqueous solution of ethanol and then 5 mL of 10% HCl solution was added. The mixture was agitated for 5 minutes. Fifty grams of methyltrimethoxysilane was dissolved in 200 mL of ethanol and 1 mL of 10% HCl was added. The mixture was agitated for 2 minutes and the they were added to 4 L of water simultaneously immediately followed by 10% NaOH solution to adjust the pH to 10. The temperature of the mixture was raised to 95° C. and then cooled to room temperature while being agitated vigorously. The insoluble particles were harvested by centrifugation and the particles were washed with 500 mL of water and 200 mL of ethanol. The products were dried at 120° C. until no further weight change was observed. The particles were crushed and sieved to obtain about 20 g of powder. The diameters of particles were about 1 micrometer and showed lambda max values at 290 nm and 340 nm. The E(1,1) values at 290 nm and 340 nm were respectively 73 $cm^{-1}\%^{-1}$ and 65 $cm^{-1}\%^{-1}$ (spectrum b in FIG. 3).

Example 5: Preparation of Polysilsesquioxane Random Copolymer from trimethoxysilylpropyl-p-methoxycinnamide and tetraethoxysilane (Particles Absorbing Both UV A and UV B)

Ten drops of concentrated HCl were added to a solution of 50 of trimethoxysilylpropyl-p-methoxycinnamide prepared in example 1 in 50 g of methanol and then agitated vigorously for 10 minutes. Fifty grams of tetraethoxysilane and 20 g of distilled water was vigorously agitated at 30° C. for about 18 hours until the odor of tetraethoxysilane almost disappeared. Two mixtures were added to 60° C. water simultaneously and then 10 g of 3-aminoprolytrimethoxysilane was added whose pH was checked to be 9. The mixture was agitated. In case the pH was not 7, 10% HCl and 10% NaOH solutions were used to adjust the pH 6-7 and then the solid products were recovered by centrifugation. The solid was re-dissolved in ethanol and insoluble parts were recovered. Approximately 15 g of particles were obtained and the UV/Vis spectrum of the particles is shown in spectrum c in FIG. 3. The particles showed lambda max values at 300 and 350 nm and E(1,1) values were respectively 90 and 110 $cm^{-1}\%^{-1}$.

Example 6: Preparation of methyldimethoxysilylpropyl-p-methoxycinnamide

Hundred grams of p-methoxycinnamic acid (Sigma-Aldrich Co.) was dissolved in 500 mL of toluene. Hundred milliliters of thionyl chloride (Oriental Steel Chemicals, Co.) was added slowly. The reaction mixture was cooled to room temperature after 18 hours reflux and then purged with nitrogen for 3 hours. Eight grams of triethylamine (Sigma-Aldrich Co.) and 100 g of 3-aminopropylmethyldimethoxysilane (Sigma-Aldrich Co.) were added. The resulting mixture was agitated for 8 hours at 60° C. and cooled to room temperature. The salt was removed by vacuum filtration and toluene was removed under vacuum to obtain methyldimethoxysilylpropyl-p-methoxycinnamide. The purity of the obtained precursor was checked using silica thin layer chromatography.

Example 7: Preparation of Polysilsesquioxane Random Copolymer from methyldimethoxysilylpropyl-p-methoxycinnamide and tetramethoxysilane (Particles Absorbing Both UV A and UV B)

Twenty grams of methyldimethoxysilylpropyl-p-methoxycinnamide was dissolved in 50 mL of methanol. Ten drops of conc. HCl was added to the solution and the solution was vigorously agitated for 3 hours. Eight grams of tetramethoxysilane was mixed with 100 mL of water and 20 drops of conc. HCl followed by 4 hours agitation. The mixtures were added to 1 L of water to obtain cloud mixture and then conc. ammonium hydroxide was added to adjust the pH to 10-11. The obtained mixture was agitated for 10 hours at ambient temperature and then the temperature was raised to 95° C. The mixture was cooled to room temperature and agitated for 18 hours. The pH of adjusted to 7 using dilute HCl and water insoluble precipitates were recovered by centrifugation and dried for 72 hours at room temperature and at 120° C. for 10 hours. The obtained product had lambda max values at 290 nm and 360 nm with E(1,1) values of 20 and 25 $cm^{-1}\%^{-1}$, respectively (spectrum d in FIG. 3)

Figure 4:
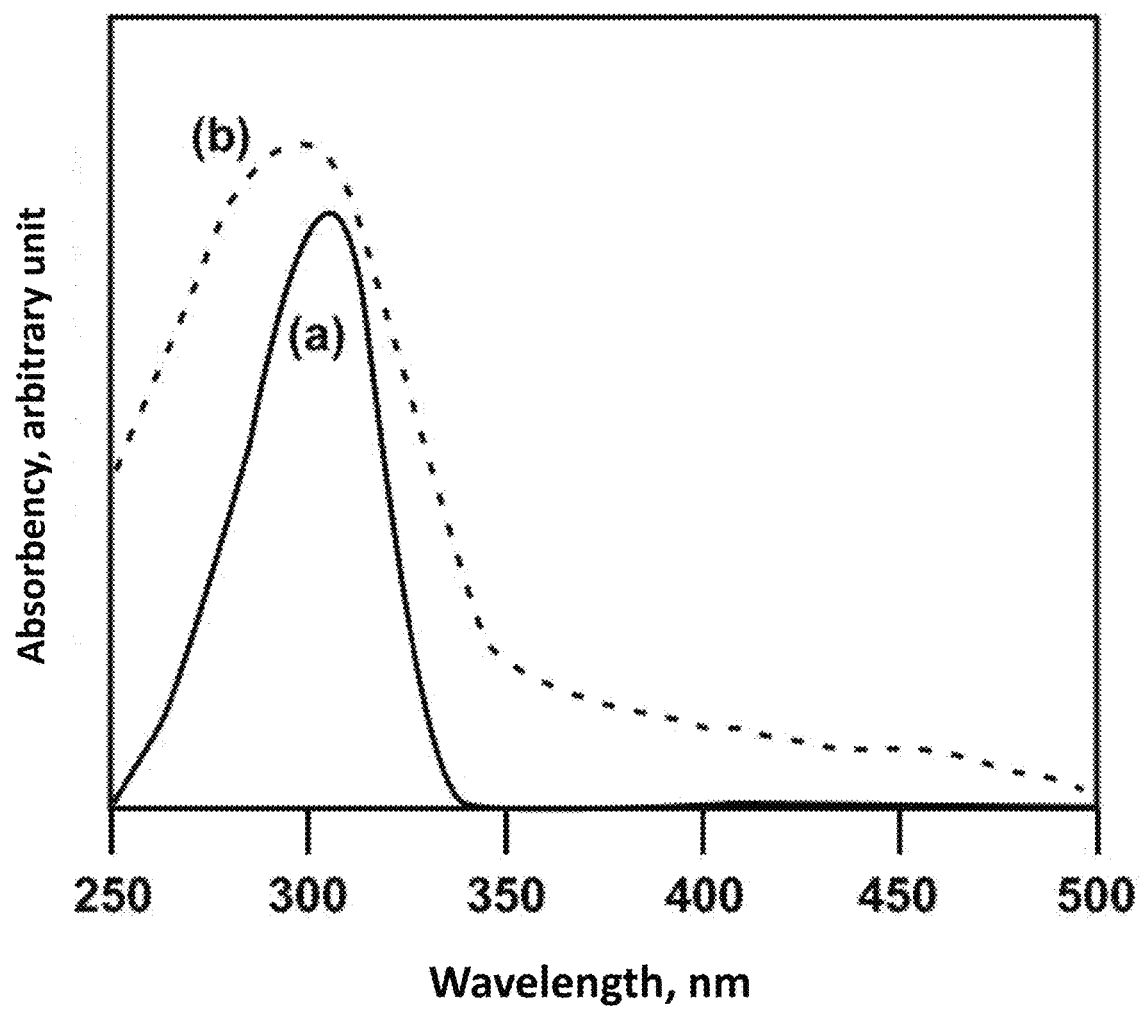
FIG. 4 shows UV/Vis absorption spectra of trimethoxysilylpropyl-p-N,N-dimethylaminobenzamide (spectrum a) prepared in example 8 and particles prepared in example 9.

Example 8: Preparation of trimethoxysilylpropyl-p-N,N-dimethylaminobenzamide Fifty grams of p-N,N-dimethylaminobenzoic acid (Sigma Aldrich Co.) was added to 500 mL of toluene while refluxing. Forty grams of thionyl chloride (Oriental Chemicals Co.) was added in portions using a dropping funnel. The reaction mixture was refluxed for 16 hours, cooled to room temperature, and then purged with nitrogen for 3 hours. Fifty-five grams of e-aminopropyltrimethoxysilane and 31 g of triethylamine (Sigma Aldrich Co.) were added slowly. The mixture was agitated for 6 hours and the salt was filtered under vacuum. Toluene was removed to obtain trimethoxysilylpropyl-p-N,N-dimethylaminobenzamide. Thin layer chromatography was used to confirm the formation of target product. The UV/Vis spectrum of the obtained precursor is shown in spectrum a in FIG. 4 that is identical to that of p-N,N-dimethylaminobenzoic acid.

Example 9: Preparation of poly(organosilicon oxide) from trimethoxysilylpropyl-p-N,N-dimethylaminobenzamide and tetraethoxysilane (comparison Product 3)

Figure 2B:
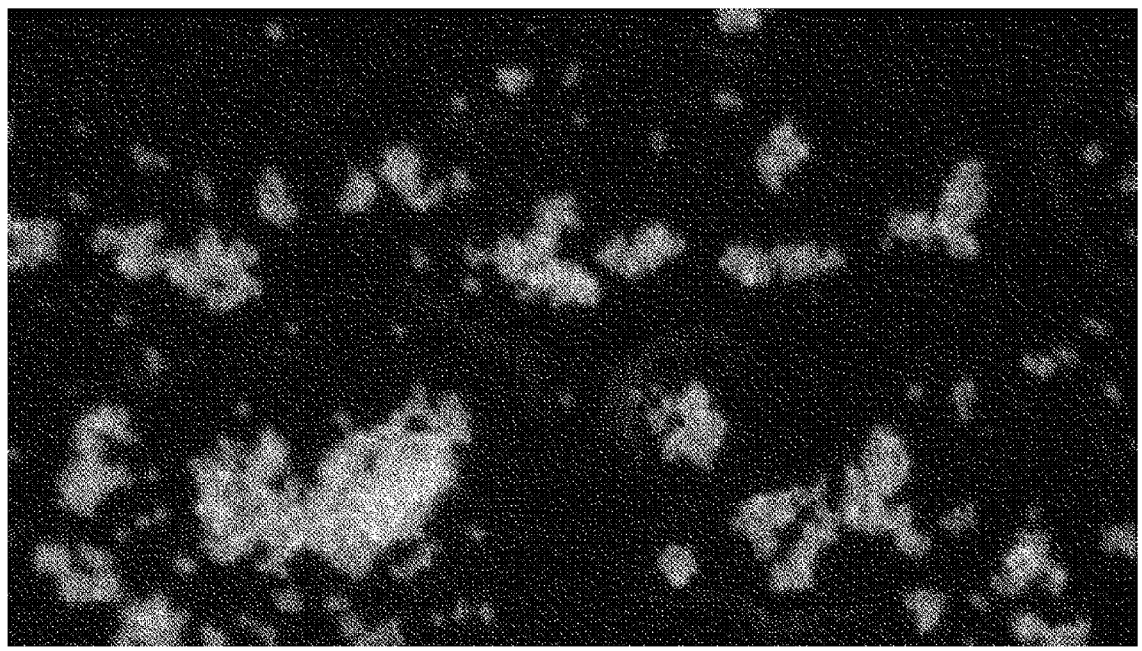
FIG. 2b shows particles observed by an optical microscope prepared in Example 2.

Ten grams of the precursor prepared in example 8 and 10 g of tetraethoxysilane were added to vigorously agitated 100 mL of NaOH aqueous solution at 60° C. in order to obtain poly(organosilicon oxide) powders from precursors containing chromophore and microstructure controllers prepared in method described in the cited. Korean Patent 1206939, The resulting colloidal solution was agitated for 12 hours and the pH of the solution was adjusted to 5-6 using HCl aqueous solution of 10 wt %. The products were agitated for additional 2 hours and then solid products were recovered by filtration. The solids were spherical particles similar to particles shown in FIG. 2 with diameters of about 1 micrometer as observed using an optical microscope. The UV/Vis spectrum of the products is shown in spectrum b in FIG. 4 that has a single lambda max at 300 nm. These results showed that particles prepared in the method described in Korean Patent 1206939 do not have excimers.

Example 10: Preparation of Polysilsesquioxane Random Copolymer from trimethoxysilylpropyl-N,N-dimethylaminobenzamide and tetramethoxysilane (Particles Absorbing both UV A and UV B)

Twenty grams of the product obtained in Example 8 (VIII) was dissolved in 20 mL of ethanol and 5 drops of concentrated. HCl was added. The mixture was vigorously agitated for 4 minutes. Eighty mL of tetramethoxysilane was added to 2 L of distilled water and agitated vigorously for 2 minutes. To the mixture of distilled water and tetramethoxysilane, the ethanol solution of the precursor agitated for 4 minutes was added at once and the pH of the mixture was raised to 9-10 using 10% aqueous solution of NaOH. The reaction mixture was heated to 80° C. as rapidly as possible and then cooled to room temperature The pH of the reaction mixture was adjusted to 7 using a dilute HCl solution and powders were recovered by centrifugation followed by drying at room temperature for 72 hours and 4 hours at 120° C. Obtained particles were similar to the particles shown in FIG. 2a with approximately 1 micrometer diameter as observed using an optical microscope. The UV/Vis spectrum is shown in spectrum e in FIG. 3. The E(1,1) at 305 nm and 370 nm were respectively 90 and 120 $cm^{-1}\%^{-1}$.

Example 11: Preparation of (2E)-3-(4-methoxyphenyl)-N-{2-[(2E)-3-(4-methoxyphenyl)-N-[3-(trimethoxysilyl)propyl]pro-2-enamido]ethyl}prop-2-enamide Fifty gram of p-N,N-dimethylaminobenzoic acid (Sigma Aldrich Co.) was added to 500 mL of refluxing toluene. Forty grams of thionyl chloride (Oriental Chemicals Co.) was added in portions using a dropping funnel attached to the refluxing condenser. After 16 hours reflux, the reaction mixture was cooled to room temperature and 37 g of N-(2-aminoethyl)-3-(trimethoxysilyl)propylamine (Acros) and 31 g of triethylamine (Sigma Aldrich Co.) was added. The reaction mixture was agitated for 6 hours at 50° C. and the resulting salt was removed by filtration. Evaporation of toluene yielded (2E)-3-(4-methoxyphenyl)-N-{2-[(2E)-3-(4-methoxyphenyl)-N-[3-(trimethoxysily)propyl]pro-2-enamido]ethyl}prop-2-enamide (XI). The formation of the product was confirmed by thin layer chromatography. The UV/Vis spectrum of the product is shown in spectrum b in FIG. 3.

Example 12: Preparation of polysilsesquioxane random copolymer from (2E)-3-(4-methoxyphenyl)-N-{2-[(2E)-3-(4-methoxyphenyl)-N-[3-(trimethoxysilyl)propyl]pro-2-enamido]ethyl}prop-2-enamide and tetraethoxysilane Twenty grams of distilled water and 10 drops of concentrated HCl were added to a solution prepared by dissolving 10 g of the product obtained in Example 11 (XI) in 50 g of isopropyl alcohol and agitated for 1 hour at room temperature. Prior to completion of 1 hour, 20 g of tetraethoxysilane, 40 mL of water, and 20 drops of concentrated HCl was mixed and agitated for 20 minutes in another container. Two solutions were added to 500 mL of water at 60° C. while being agitated vigorously. The pH of the reaction mixture was adjusted to 10 using 10% aqueous solution of NaOH. The colloidal solution was heated to 95° C. and then cooled to room temperature. Obtained powders were dried at room temperature for 72 hours and then dried at 120° C. Approximately 6 g of powders were obtained and optical microscopic observation showed the particles were spherical with diameters of approximately 1.5 micrometers. These particles showed lambda max values at 290, 350, and 380 nm. E(1,1) values at each lambda max values were respectively 40, 38, and 32 $cm^{-1}\%^{-1}$. The UV/Vis spectrum is shown in spectrum f in FIG. 3.

Example 13: Preparation of (2E)-3-(4-methoxyphenyl)-N-{2-[(2E)-3-(4-methoxyphenyl)-N-2-[(2E)-3-(4-methoxyphaynl)-N-[3-(trimethoxysilyl)propyl]pro-2-enamido]ethylprop-2-enamido]ethyl}prop-2-enamide One hundred grams of p-methoxycinnamic acid (Sigma Aldrich Co.) was added to 500 mL of refluxing toluene. Fifty grams of thionyl chloride (Oriental Chemicals Co.) was added in small portions using a dropping funnel attached to the refluxing condenser. The reaction mixture was refluxed for 16 hours and then all volatile compounds were removed under vacuum. The obtained product was dissolved in 200 mL of toluene to get transparent solution and 55 g of N-(3-triomethoxysilylpropyl)diethylenetriamine (Across) and 56 g of trimethylamine (Sigma Aldrich Co.) were added slowly. The reaction mixture was agitated for 6 hours and the resulting salt was removed by filtration. Toluene was removed to obtain (2E)-3-(4-methoxyphenyl)-N-{2-[(2E)-3-(4-methoxyphenyl)-N-2-[(2E)-3-(4-methoxyphaynl)-N-[3-(trimethoxysilyl)propyl]pro-2-enamido]ethylprop-2-enamido]ethy}prop-2-enamide. Formation of the product was confirmed using thin layer chromatography.

Example 14: Preparation of poly(organosilicon oxide) from (2E)-3-(4-methoxyphenyl)-N-{2-[(2E)-3-(4-methoxyphenyl)-N-2-[(2E)-3-(4-methoxyphaynl)-N-[3-(trimethoxysilyl)propyl]pro-2-enamido]ethylprop-2-enamido]ethy}prop-2-enamide and tetraethoxysilane (Particles absorbing both UV A and UV B)

Ten grams of the product obtained in example 13 (XIII) was dissolved in 30 g of isopropyl alcohol and 40 g of tetraethoxysilane was added. To the mixture 2 g of 3-aminopropyltriethoxysilane was added and the whole mixture was mixed with 2 L of water. Using concentrated ammonium hydroxide solution, the pH of the colloid was adjusted to 9-10 followed by agitating for 18 hours to obtain spherical solid products. The pH of the product mixture was adjusted to 5-6 using 10% aqueous solution of HCl and insoluble solid products were recovered by centrifugation. The product was dried at room temperature and then ground to obtain final products of spherical shape. The diameters of particles were approximately 2 micrometers, E(1,1) at 295, 360, and 390 nm were 44, 41, and 38 $cm^{-1}\%^{-1}$ (Spectrum g in FIG. 3).

Example 15: Preparation of 4-(dimethoamino)-N-(2-{1-[4-(dimethylamino)phenyl]-N-[2-{1-[4-(dimethylamino)phenyl]-N-[3-(trimethoxysilyl)propyl]formamindo}ethyl]formamido}ethyl)benzamide Fifty grams of p-N,N-dimethylaminobenzoic acid (Sigma Aldrich Co.) was added to 500 mL of toluene while refluxing. Forty grams of thionyl chloride (Oriental Chemicals Co.) was added in small portions using a dropping funnel attached to the refluxing condenser. The reaction mixture was refluxed for 16 hours and then all to volatile materials were removed under vacuum. To a transparent solution obtained dissolving the products in 200 mL of toluene, 30 g of N-(3-trimethoxysilylpropyl)diethylenetriamine (Acros) and 31 g of trimethylamine (Sigma Aldrich Co.) were slowly added. The reaction mixture was agitated for 6 hours and the resulting salt was removed by vacuum filtration. Toluene was evaporated to obtain 4-(dimethoamino)-N-(2-{1-[4-(dimethylamino)phenyl]-N-[2-{1-[4-(dimethylamino)phenyl]-N-3-(trimethoxysilyl)propyl]formamido}ethyl]formamido}ethyl)benzamide (XV). Formation of the product was confirmed using thin layer chromatography.

Example 16: Preparation of poly(organosilicon oxide) from Preparation of 4-(dimethoamino)-N-(2-{1-[4-(dimethylamino)phenyl]-N-[2-{1-[4-(dimethylamino)phenyl]-N-[3-(trimethoxysilyl)propyl]formamindo}ethyl]formamido}ethyl)benzamide and tetraethoxysilane (Powders absorbing both UV A and UV B)

To a solution prepared by dissolving 20 g of the product prepared in example 15 (XV) in 200 mL of ethanol, 30 g of tetraethoxysilane was added. The pH of the mixture was adjusted to 9-10 using 10% NaOH aqueous solution and agitated vigorously at room temperature for 12 hours. The pH was adjusted to 6-7 using 10% HCl aqueous solution and the product was recovered by centrifugation and dried at room temperature to obtain solid particles after grinding. The shape of obtained powders were irregular with sizes of approximately 2-5 micrometers. The powders had lambda max at 300 and 390 nm with E(1,1) of 20 and 25 $cm^{-1}\%^{-1}$, respectively (spectrum h in FIG. 3.)

Example 17: Preparation of poly(organosilicon oxide) from trimethoxysilylpropyl-p-methoxycinnamide and phenyltrimethoxysilane (comparison particle 3)

Ten drops of concentrated hydrochloric acid were added to a solution of 50 g of trimethoxysilylpropyl-p-methoxycinnamide (I) in 50 g of methanol and the mixture was agitated vigorously for 10 minutes. A mixture prepared by mixing 20 g of phenyltrimethoxysilane and 20 mL of water was agitated at 30° C. for 18 hours when the mixture became homogeneous. Two mixtures were added to 60° C. water simultaneously and 10 g of 3-aminopropyltrimethoxysilane was added immediately. The reaction mixture was agitated for 10 hours. The pH of the mixture was adjusted to 7 using concentrate HCl and solid products were recovered by centrifugation, and dried at room temperature for 72 hours to obtain 9 g of particles. Optical microscopic observation showed diameters of the particles were approximately 1 micrometer. The particles showed a single lambda max at 295 nm with E(1,1) of 46 $cm^{-1}\%^{-1}$. These results showed that phenyltrimethoxysilane alone does not function as microstructure controller.

Example 18: Preparation of poly(organosilicon oxide) from trimethoxysilylpropyl-p-methoxycinnamide, tetraethoxysilane, and phenyltrimethoxysilane (Particles absorbing both UV A and UV B)

To a solution of 50 g of trimethoxysilylpropyl-p-methoxycinnamide in 50 g of methanol, 10 drops of concentrated. HCl was added and the mixture was agitated vigorously for 10 minutes. A mixture of 10 g of phenyltrimethoxysilane and 10 mL of distilled water was vigorously agitated at 30° C. for 18 hours when the mixture became homogeneous. A mixture of 20 of tetramethoxysilane, 20 mL of 50% aqueous solution of ethanol, and 10 drops of concentrated HCl was annealed for 10 minutes. Three mixtures were added to 60° C. water simultaneously, and then 10 g of 3-aminopropyltrimethoxysilane was immediately added and then the mixture was agitated for 10 hours. The pH of the mixture was adjusted to 7 using dilute aqueous solution of HCl and the solid materials were recovered by centrifugation to obtain 24 g of particles after drying at room temperature. The particle had diameters of approximately 1 micrometer. The particles showed lambda max values at 300 nm and 345 nm with $E(1,1)$ values of 30 and 34 $cm^{-1}\%^{-1}$.

Example 19: Thermal Stability of Polysilsesquioxane Random Copolymer Obtained from trimethoxysilypropyl-p-methoxycinnamide and tetraethoxysilane Ten grams of particles obtained in Example 7 was heated at 120° C. in the air for 12 hours. The $E(1,1)$ values at 300 nm and 350 nm were 89 and 112 $cm^{-1}\%^{-1}$ that were almost identical to those of original particles and there was no change in color.

Example 20: Stability against solvent of polysilsesquioxane random copolymer prepared from trimethoxysilylpropyl-p-methoxycinnamide and tetraethoxysilane Ten grams of particles prepared in Example 7 were dispersed in 100 mL of ethanol and then kept for 12 hours at 70° C. $E(1,1)$ values of the recovered particles at 300 nm and 350 nm were respectively 88 and 109 $cm^{-1}\%^{-1}$ that were almost identical to those of original particles showing that absorbency of the particles was not affected by the solvent.

Having described a preferred embodiment of the present invention, it is to be understood that variants and modifications thereof falling within the spirit of the invention may become apparent to those skilled in this art, and the scope of this invention is to be determined by appended claims and their equivalents.

The invention claimed is:

1. A crosslinked polysilsesquioxane random copolymer that absorbs both UV A and UV B as a result of excimer or exciplex formation between chromophores which is prepared from a mixture comprising (i) monomer 1 as a silsesquioxane monomer which is selected from the group consisting of Chemical Structure 1 to 3 and (ii) monomer 2 which is selected from the group consisting of tetraalkoxysilane, alkyltrialkoxysilane, aminoalkyltrialkoxysilane, aryltrialkoxysilane, dialkyldialkoxysilane, diaryldialkoxysilane, arylalkyldialkoxysilane and mixtures thereof serving as a microstructure controller, <Chemical Structure 1>

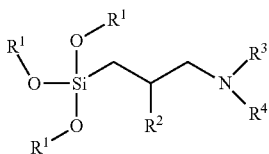

<Chemical Structure 2>

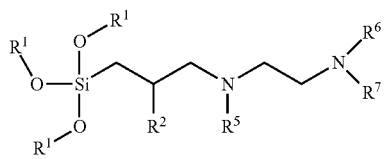

<Chemical Structure 3>

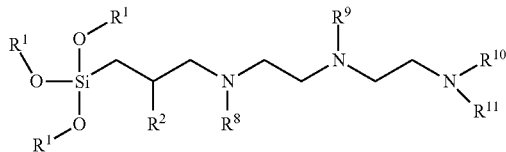

$R^1$ is independently a $C_1$-$C_{10}$ alkyl group, $R^2$ is hydrogen or a $C_1$-$C_{10}$ alkyl group, $R^3$-$R^4$ in Chemical Structure 1, $R^5$-$R^7$ in Chemical Structure 2, and $R^8$-$R^{11}$ in Chemical Structure 3 is independently (a) hydrogen or (b) a UV B absorbing group (chromophore) selected from a group consisting of cinnamoyl group, cinnamoyl group substituted with alkoxy group, benzoyl group, benzoyl group substituted with alkylcarboxyl group, benzoyl group substituted with dialkylamino group, benzylidenecamphor sulfonyl group, salicyloyl group, salicyloyl group substituted with acetyl group, and coumarin carboxyl group, and at least one of $R^3$-$R^4$ in Chemical Structure 1, at least one of $R^5$-$R^7$ in Chemical Structure 2, and at least one of $R^8$-$R^{11}$ in Chemical Structure 3 is a group selected from the UV B absorbing groups listed above.

2. The crosslinked polysilsesquioxane random copolymer according to claim 1, wherein when one of $R^3$-$R^4$ in Chemical Structure 1, one of $R^5$-$R^7$ in Chemical Structure 2, one of $R^8$-$R^{11}$ in Chemical Structure 3 is a UV B absorbing group listed above, the others are hydrogen.

3. The crosslinked polysilsesquioxane random copolymer according to claim 1, wherein the tetraalkoxysilane, alkyltrialkoxysilane, aminoalkyltrialkoxysilane, aryltrialkoxysilane, dialkyldialkoxysilane, diaryldialkoxysilane, and arylalkyldialkoxysilane contain C1-C10 alkyl group, C1-C10 alkoxy, or C6-C10 aryl groups.

4. The crosslinked polysilsesquioxane random copolymer according to claim 1, wherein the composition of monomer 1 and monomer 2 is from 100:1 to 1:5 by weight.

5. A method for preparing crosslinked polysilsesquioxane random copolymers including steps:

(a) individually dissolving (i) silsesquioxane monomer 1 selected from the group consisting of compounds with Chemical Structures 1 to 3 shown below, and (ii) monomer 2 selected from a group of tetraalkoxysilane, alkyltrialkoxysilane, aminoalkyltrialkoxysilane, aryltrialkoxysilane, dialkyldialkoxysilane, diaryldialkoxysilane, arylalkyldialkoxysilane and mixtures thereof serving as a microstructure controller; and (b) reacting the solutions of monomer 1 and monomer 2 by mixing them together <Chemical Structure 1>

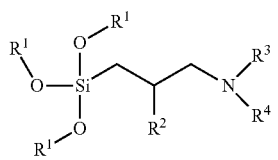

-continued

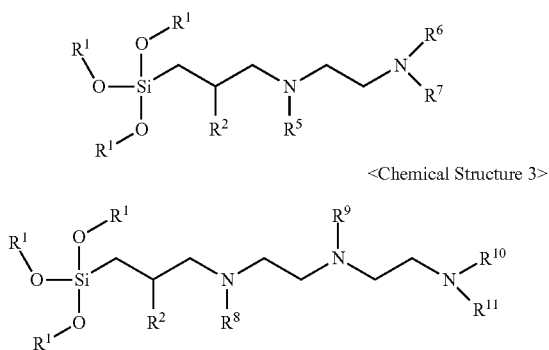

<Chemical Structure 2>

<Chemical Structure 3>

$R^1$ is independently a $C_1$-$C_{10}$ alkyl group, $R^2$ is hydrogen or a $C_1$-$C_{10}$ alkyl group, $R^3$-$R^4$ in Chemical Structure 1, $R^5$-$R^7$ in Chemical Structure 2, $R^8$-$R^{11}$ in Chemical Structure 3 is independently (a) hydrogen or (b) a UV B absorbing group selected from a group consisting of cinnamoyl group, cinnamoyl group substituted with alkoxy group, benzoyl group, benzoyl group substituted with alkylcarboxyl group, benzoyl group substituted with dialkylamino group, benzylidenecamphor sulfonyl group, salicyloyl group, salicyloyl group substituted with acetyl group, and coumarin carboxyl group, and at least one of $R^3$-$R^4$ in Chemical Structure 1, at least one of $R^5$-$R^7$ in Chemical Structure 2, and at least one of $R^8$-$R^{11}$ in Chemical Structure 3 is a group selected from the UV B absorbing groups listed above.

6. The method according to claim 5, wherein when one of $R^3$-$R^4$ in Chemical Structure 1, one of $R^5$-$R^7$ in Chemical Structure 2, one of $R^8$-$R^{11}$ in Chemical Structure 3 is a UV B absorbing group listed above, the others are hydrogen.

7. The method according to claim 5, wherein the microstructure controllers are selected from the group consisting of tetraalkoxysilane, alkyltrialkoxysilane, aminoalkyltrialkoxysilane, aryltrialkoxysilane, dialkyldialkoxysilane, diaryldialkoxysilane, and arylalkyldialkoxysilane and which comprises a $C_1$-$C_{10}$ alkyl group, a $C_1$-$C_{10}$ alkoxy, or a $C_6$-$C_{10}$ aryl group.

8. The method according to claim 5 wherein the tetraalkoxysilane is selected from the group consisting of tetramethoxysilane, tetraethoxysilane, tetrakis[2-(2-methoxyethoxy)ethoxy]silane, and tetrakis(methoxethoxy)silane.

9. The method according to claim 5 wherein the alkyltrialkoxysilane is selected from the group consisting of propyltrimethoxysilane, ethyltrimethoxysilane, methyltrimethoxysilane, propyltriethoxysilane, ethyltriethoxysilane, and methyltriethoxysilane.

10. The method according to claim 5 wherein the aminoalkyltrialkoxysilane is selected from the group consisting of aminomethyltrimethoxysilane, aminomethyltriethoxysilane, aminoethyltrimethoxysilane, aminoethyltriethoxysilane, aminopropyltrimethoxysilane, and aminopropyltriethoxysilane.

11. The method according to claim 5 wherein the aryltrialkoxysilane is selected from the group consisting of naphthyltrimethoxysilane, naphthyltriethoxysilane, phenyltrimethoxysilane, and phenyltriethoxysilane.

12. The method according to claim 5 wherein the dialkyldialkoxysilane is selected from the group consisting of propylmethyldimethoxysilane, ethylmethyldimethoxysilane, dimethyldimethoxysilane, methylpropyldiethoxysilane, diethyldiethoxysilane, and dimethyldiethoxysilane.

13. The method according to claim 5 wherein the diaryldialkoxysilane is selected from the group consisting of diphenyldimethoxysilane and diphenyldiethoxysilane.

14. The method according to claim 5 wherein the arylalkydialkoxysilane is selected from the group consisting of phenylmethyldimethoxysilane, phenylmethyldiethoxysilane, phenylethyldimethoxysilane, and phenylethyldiethoxysilane.

15. The method according to claim 5 wherein the solvent in step (a) is independently selected from a group consisting of methanol, ethanol, isopropanol, butanol, ethyleneglycolmethyl ether, ethyleneglycolethyl ether, propyleneglycolethyl ether, diethyl ether, tetrahydrofuran, dioxane, acetone, methylethylketone, water, and mixtures thereof.

16. The method according to claim 5, wherein the solvent in step (b) is acidic (pH lower than 7).

17. The method according to claim 5, wherein the solvent in step (b) is basic (pH higher than 7).

18. The method according to claim 5, wherein step (b) is carried out at a temperature of 15-99° C.

19. The method according to claim 18, further comprising a step of adjusting the temperature to room temperature.

20. The method according to claim 19, wherein the pH is adjusted to 5-8.

21. The method according to claim 20, further comprising a recovery step and a drying step.

22. A crosslinked polysilsesquioxane random copolymer according to claim 5 which absorbs both UV A and UV B as a result of excimer or exciplex formation.

* * * * *